United States Patent [19]
Syed et al.

[11] Patent Number: 6,007,585
[45] Date of Patent: Dec. 28, 1999

[54] HAIR BRIGHTENING SYSTEM

[75] Inventors: Ali N. Syed, Inverness; Wagdi W. Habib, Barrington; Longsheng Hu, Chicago, all of Ill.

[73] Assignee: Avlon Industries, Inc., Bedford Park, Ill.

[21] Appl. No.: 09/211,918

[22] Filed: Dec. 15, 1998

Related U.S. Application Data

[63] Continuation-in-part of application No. 08/950,847, Oct. 15, 1997, abandoned.

[51] Int. Cl.$^6$ ................................ A61K 7/13; A45D 7/04
[52] U.S. Cl. ........................ 8/432; 8/405; 8/426; 8/431; 8/127.51; 132/204; 132/205; 132/208
[58] Field of Search ................................ 8/405, 406, 431, 8/107, 110, 426, 432, 127.51; 132/203, 204, 205, 208; 252/187.31, 188.21, 188.22; 424/62, 70.2, 70.5, 70.4, 70.6

[56] References Cited

U.S. PATENT DOCUMENTS

| | | | |
|---|---|---|---|
| 3,773,056 | 11/1973 | Kalopissis et al. | 132/209 |
| 3,793,214 | 2/1974 | O'Neil et al. | 510/147 |
| 3,811,835 | 5/1974 | Gallup et al. | 8/127.6 |
| 3,892,845 | 7/1975 | Cunningham et al. | 424/62 |
| 4,058,131 | 11/1977 | Crawford et al. | 132/7 |
| 4,279,653 | 7/1981 | Makishima et al. | 106/22 |
| 4,781,724 | 11/1988 | Wajaroff et al. | 8/432 |
| 4,822,604 | 4/1989 | Knoll et al. | 514/864 |
| 4,927,627 | 5/1990 | Schrader et al. | 424/62 |
| 5,051,252 | 9/1991 | Schultz et al. | 424/71 |
| 5,102,655 | 4/1992 | Yohihara et al. | 424/62 |
| 5,293,885 | 3/1994 | Darkwa et al. | 132/209 |

FOREIGN PATENT DOCUMENTS

| | | |
|---|---|---|
| 2-76807 | 3/1990 | Japan . |
| 9-151121 | 6/1997 | Japan . |

OTHER PUBLICATIONS

English language translation of JP–76807, San–El Chemical Co., pp. 1–80, Jun. 1988.

*Primary Examiner*—Caroline D. Liott
*Attorney, Agent, or Firm*—Olson & Hierl, Ltd.

[57] ABSTRACT

A hair brightening process and aqueous hair brightening compositions therefor are disclosed effective for removing discolorations from hair which is undesirably discolored due to chemical processes and environmental exposure or natural aging to provide a substantially more natural tone. The hair brightening compositions of the invention comprise certain hair brightening activating salts and organic colorants as active brightening ingredients which surprisingly remove discoloration without imparting an unnatural tone to the hair. The inventive hair brightening compositions provide a significant improvement over conventional prior-art hydrogen peroxide-based hair brightening compositions in effectiveness, are less damaging to the hair, and more varied in their useful product forms. The invention is also directed to compositions and methods for alkali relaxing and brightening hair, especially naturally gray hair, and single-use kits comprising the inventive hair brightener compositions.

16 Claims, No Drawings

HAIR BRIGHTENING SYSTEM

CROSS-EFERENCE TO RELATED APPLICATIONS

This application is a continuation-in-part of U.S. Ser. No. 08/950,847, filed Oct. 15, 1997.

FIELD OF THE INVENTION

This invention relates generally to the chemical processing of hair fibers and more particularly to a hair brightening composition and process for improving the tone of and removal of discolorations from alkali relaxed hair. The invention also relates to a composition and process which provides a less damaging means of removing discolorations in hair than conventional hydrogen peroxide containing hair brightening compositions.

BACKGROUND OF THE INVENTION

The growing demand for new hairstyles has shaped a lucrative industry for salons and hair stylists. Further, the ability to change the appearance of one's hair through chemical processes is important to both men and women. More specifically, it is important for both men and women to be able to chemically relax or to permanently wave the hair so that they may keep up with the rapidly changing hair style fashion in the hair industry. In some instances, such chemical processes, and alkali hair relaxers in particular, have the undesirable and very noticeable effect of discoloring of the natural underlying color of hair, particularly naturally blonde and gray hair. In addition, environmental effects, such as exposure to sun or smoke and like pollutants, may also cause discolorations. Also, in many individuals, the natural color of the hair may discolor with age or illness and develop an undesirable tone even without chemical processing or environmental exposure.

In general, the discoloration of natural gray and natural blonde hair due to natural processes, environmental exposure, and chemical alkaline waving or relaxing processes is a visually observable undesirable yellowish tone on the white unpigmented fibers, although other tonal alterations are observed, such as brassiness. Discolored hair fibers also appear dull, drab and lackluster, whereas in non-discolored hair, the natural underlying tone of the hair fibers provides a desirable natural bright tone with highlights to the hair. For purposes of this invention, the term "discolorations" and grammatical variations thereof with reference to hair means discolorations such as described herein including, but not limited to, yellow, brown, blue and purple tones, brassiness and dullness.

Alkali hair relaxing compositions may employ strongly alkaline relaxing agents such as inorganic alkali metal hydroxides such as, but not limited to, sodium hydroxide, potassium hydroxide, lithium hydroxide, and calcium hydroxide or oxides thereof capable of forming hydroxides in water; or relatively strong organic bases such as, but not limited to, guanidine, guanidine hydroxide or quaternary ammonium hydroxide. These chemicals are highly caustic with a pH of above approximately 12, and at such high alkalinity alkali relaxers may undesirably alter and discolor the natural tone of human hair, especially noticeable on naturally white hair fibers. Other non-alkaline relaxing compositions may also cause discoloration of the hair.

Alkali hair relaxers containing sodium hydroxide are especially popular and are commonly known as lye-type relaxers. Some lye-type hair relaxers have included keratin-disulfide reducing agents in an attempt to limit the amount of discoloration that occurs during alkali relaxing. For example, compositions with available sulfhydyrol groups, such as dimercaptoadipic acid or cysteine, have been included in the relaxer creme. However, these products do not work as well as needed and are thus limited in use, for example, as part of a relaxing process.

Waving compositions effect a substantially lasting transformation of straight hair into waved hair. Often, such waving systems utilize reducing agents comprised of thiols, including, but not limited to, thioglycolic acid, thiolactic acid, cysteine, thioglycerol, thioglycolic hydroxide, thioglycolamide and glycerol monothioglycolate. These waving composition are alkaline and typically have a high pH above 8 to about 10. Such alkaline waving compositions also may undesireably alter and discolor the natural tone of human hair. In addition, non-thiol waving compositions may also cause discoloration of the hair.

Thus, there is a need and desire for a composition and process to brighten the tone of alkali relaxed and waved hair which has become discolored to restore a more natural appearance. One commercially available hair brightening system uses hydrogen peroxide as a hair brightening agent. Although this system successfully brightens the tone of discolored hair, hydrogen peroxide produces undesirable side effects which include a significant decrease in the tensile strength of the hair, making the hair more susceptible to chemical or combing damage, resulting in hair with a frizzy and damaged appearance, an increase in the risk of irritation or burning of the scalp or skin, an increase in risk of chemical damage to the hair upon later chemical processing, and bleaching of the natural underlying color of the pigmented hair of individuals with brown, red or black hair.

Other approaches used to brighten hair, generally natural gray or white hair, include applying a temporary or semi-permanent hair coloring, usually applied as a violet or blue rinse to mask the underlying discoloration. However, since such color rinses are typically applied and left on the hair, such rinses can produce further visually unsatisfactory tones, such as unnatural purples and blues, and can leave an undesirable dull coating on the hair.

Thus, conventional hydrogen peroxide-based brightening systems suffer from the disadvantages of reduction in tensile strength of the hair, structural damage to the hair, irritation or burning to the scalp, and color rinses unsatisfactorily color the hair.

Accordingly, there is still an ongoing need for a hair brightening composition that overcomes hair discoloration problems resulting from the use of alkaline chemical processing products or environmental exposures, which minimizes apparent damage to the hair and minimizes loss of tensile strength of the hair. There is also a need and desire for easy-to-use improved compositions which brighten the hair that can be employed during waving or relaxing hair processes which brighten the hair.

The inventive hair brightening system answers that need. Further the inventive hair brightening system and methods for brightening hair can be used as an adjunct to an alkali relaxing process.

SUMMARY OF THE INVENTION

The invention is directed to hair brightening compositions in a variety of useful forms which are effective in removing discolorations from hair to provide a substantially more natural tone, particularly to gray (having up to 100% white fibers) or blonde hair which is naturally discolored as well as hair which is discolored due to chemical processes and environmental exposures.

The inventive aqueous hair brightening compositions comprise water having dissolved therein on a total composition basis (a) about 0.001 to about 10 weight percent of a hair brightening activator salt and (b) about 0.00001 to about 1 weight percent of an organic colorant selected from anthraquinone and triphenylmethane colorants and mixtures thereof. Preferred compositions of the invention comprise as active brightening ingredients hair brightening activator salts that are oxidizing agents, including but not limited to, alkali metal salts of bromate, chlorate and the like; reducing salts of alkali metal sulfite, bisulfite, hydrosulfite and the like, and cosmetically acceptable blue or violet certified organic coloring agents used alone or in combination.

Preferred hair brightening activator salts are sodium or potassium salts of bromate and chlorate. Sodium bromate is particularly preferred. Preferred anthraquinone organic colorants are selected from the group consisting of D&C Violet #2, External D&C Violet #2, and a preferred triphenylmethane organic colorant is FD&C Blue #1.

A particularly preferred hair brightener composition was in the form of a shampoo containing on a total composition basis about 1 to about 2 weight percent sodium bromate, about 0.01 to about 0.05 weight percent of organic colorant and having a pH in the range of about 5 to about 7. Preferably, the shampoo was a two-part product maintaining in one part the sodium bromate separate from the organic colorant and mixing the two parts together substantially immediately before use.

The invention is also directed to compositions and methods for relaxing and brightening compositions and methods, and single-use kits for relaxing hair comprising the brighteners of the invention.

In salon studies, by the time the hair brightener compositions of the invention were applied to and distributed through the hair (particularly through the discolored portions), the tone of the hair was visibly and desirably brightened to a tone substantially near to natural. Discolored hair fibers were generally brightened, and their natural attractive bright highlights were visibly and dramatically restored.

The hair brightening compositions of the invention provide a significant improvement over conventional prior-art hydrogen peroxide-based brightening compositions in that they are more effective, less damaging to the hair, and more varied in their product forms, including but not limited to shampoo, emulsions, lotions, activator solutions, conditioners, cremes or gels and like other cosmetically acceptable formulations for use on hair.

Other benefits and advantages of the invention will become apparent upon reading the following detailed description.

DETAILED DESCRIPTION OF THE INVENTION

As used herein, the term "discolorations" in reference to hair, "discolored hair" and grammatical variations thereof refers to natural blonde and natural gray hair (typically having more than 10% white fibers) whose natural underlying tone has been altered to an undesirable, unnatural discoloration such as, but not limited to, a tone that is yellow, greenish, golden, brown, blue or purple and the like, or has a brassiness in appearance and is visually dull and lackluster. The term "brightened hair" and grammatical variations thereof means that the tone of hair which has discolorations as previously defined has been visibly restored to a substantially more natural tone and luster.

The term "hair brightener" and grammatical variations thereof is used herein to denote a composition capable of visibly restoring a more natural appearance to the tone of gray or blonde (frosted, decolorized or highlighted) hair whose natural appearance has become undesirably dulled, yellowed or has acquired a brassiness from the use of chemical hair products, or from environmental exposure or natural aging. In particular, the inventive hair brightener compositions restore more natural tones to such hair without damaging or bleaching the hair and can be used substantially immediately before or following an alkali relaxer process or in between alkali relaxer treatments or as post-wave treatments.

The term "hair brightener activator salt" as used herein refers to alkali metal salts that are normally classed as oxidizing or reducing salts which surprisingly remove discoloration from alkali relaxed or waved hair with substantially minimal or no damage to the hair when used in the compositions of this invention.

For convenience, the term "alkali relaxer," as used herein refers to hair relaxers that contain strong inorganic or organic bases and thus are highly alkaline (pH>11) and includes single part alkali metal hydroxide relaxers and two-part organic base relaxers, commonly called no-lye type relaxers. Single part alkali metal hydroxide relaxers commercially contain sodium hydroxide (lye-type) or potassium hydroxide or lithium hydroxide as the active hair relaxing inorganic base and such products are applied directly from the container. Two-part organic base relaxers generally employ guanidine and guanidine hydroxide as the active hair relaxing organic base which is commercially prepared immediately before use by mixing together one formulation part containing calcium hydroxide and a second solution part containing a guanidine salt to generate the free organic base in situ.

The compositions according to the invention comprise as active hair brightening agents, (a) a hair brightening activator salt selected from oxidizing salts of sodium or potassium bromate, sodium or potassium chlorate and the like, or reducing salts of sodium or potassium sulfite, sodium bisulfite, sodium hydrosulfite and the like and (b) a hair brightening organic coloring agent selected from anthraquinone-type coloring agents, preferably, but not limited to, D&C Violet #2 (C.I. 60,725) or External D&C Violet #2 (C.I. 60,730) and triphenylmethane-type coloring agents, such as FD&C Blue #1 (C.I. 42,090); and combinations thereof. A preferred hair brightening composition contains at least one of the above-named oxidizing salts, and at least one of the above-named organic coloring agents, in a cosmetically acceptable medium. A particularly preferred hair brightening composition contains sodium bromate.

A preferred hair brightener embodiment can be formulated as a homogeneous aqueous composition or can be a two-part product that is mixed for use substantially immediately before use. A particularly preferred hair brightener embodiment is in the form of a conditioning shampoo or hair conditioner product. Most preferably the conditioning shampoo is a two-part product in which one part comprises an aqueous solution of the hair brightener activator salt and the second part comprises at least one organic colorant in combination with the remaining components of the shampoo formulation and the two parts are mixed substantially immediately before use in sufficient amounts to effect the desired amount of hair brightening.

Useful cosmetic media may include, but are not limited to, shampoos, emulsions, gels, activator solutions, conditioners, cremes, lotions, and like cosmetically acceptable media which may be rinsed from the hair. The composition preferably may also comprise one or more of the following ingredients: preservatives, chelating agents, antistatic agents, foaming agents, solubilizers, opacifiers, conditioning agents, at least one cationic polymer, protein, deswelling agents, mineral oil and fragrance. Those skilled in the cosmetic arts are familiar with conventional ingredients which are commercially available from a number of sources. Descriptions of and suppliers of conventional ingredients can readily be found in a number of trade publications. For convenience, ingredients generally will be referred to by the industry recognized standardized designations given them in the *International Cosmetic Ingredient Dictionary*, Sixth Edition, published by The Cosmetic, Toiletry, and Fragrance Association, Washington, DC (1995) commonly referred to as "INCI" names.

The kits of the invention include a single-use application of either any commercially available alkali relaxer (such as Affirm® Creme Hair Relaxers commercially available from Avlon Industries, Inc., Bedford Park, Ill.) or alternatively any commercially available wave composition (such as Syntonics® Multiplex® Wave Solution, commercially available from American Chemical Industries, Bedford Park, Ill.), plus one or more of the brightening compositions of the invention, incorporated into the relaxer or wave composition or in any suitable media apart from the relaxer or wave composition. The kits of the invention may further optionally comprise any commercially available hair protectorant composition such as Preservo™ protectorant (commercially available from Avlon Industries, Inc., Bedford Park, Ill.). The kits of the invention may also optionally include one or more of the following: gloves, applicators, a hair cap or cover, and such other accessories as are desirable for the subject hair process.

The hair brightening compositions of the invention achieve the surprising result of causing significantly less damage to alkali relaxed hair than conventional hydrogen peroxide-based brightening compositions, as shown in Table 1, of Example 16 below. This allows the hair brightening compositions of the invention to be used repeatedly, or to be used in more than one form in the same treatment (such as, but not limited to, for example, as a hair brightening shampoo prior to relaxing, and again used as part of the relaxing process, after or in place of the post-relaxer shampoo).

Surprisingly, a significant brightening is observed at relatively low concentrations of active brightening ingredients in the brightening compositions of the invention without causing bleaching or other visible damage to the hair, over a physiologically tolerable pH of less than about 9, preferably in the range of about 2 to about 8.5, more preferably in a range of about 5 to about 7.

Also surprisingly, we have discovered that discolored hair was brightened by application of a post-relaxer or a post-wave hair brightener composition comprising one or more of the organic colorants, D&C Violet #2, External D&C Violet #2 or FD&C Blue #1, as the active hair brightening ingredient, present at relatively low concentrations in the range of about 0.00001 weight percent to about 1 weight percent, more preferably in the range of about 0.0001 to about 0.005 weight percent without imparting an unnatural tone to the hair, particularly when used in combination with sodium bromate.

Yet another surprising finding was that hair brightening compositions comprising oxidizing chlorate salts as brightening agents also successfully removed discolorations from alkali relaxed or waved discolored hair. A preferred embodiment of the present invention comprises an aqueous solution of potassium or sodium chlorate at a concentration in the range of about 0.1–10%, preferably about 1–5%, as the oxidizing brightening agent.

Another surprising finding was that discolored hair was more desirably brightened when combinations of sodium bromate, and organic colorant (D&C Violet #2 and External D&C Violet #2 or FD&C Blue #1) as active ingredients were applied to the hair than when the sodium bromate or organic colorant was the sole active ingredient. Used in combination with the organic colorants, the sodium bromate preferably is at a concentration in the range of about 0.5 weight percent to about 5 weight percent, preferably about 1 to about 2 weight percent, with the concentration of active organic colorant in the range of about 0.00001 weight percent to about 0.75 weight percent, preferably about 0.0001 weight percent to about 0.3 weight percent and more preferably about 0.01 weight percent and about 0.05 weight percent. Surprisingly, this combination of active brightening ingredients not only brightened the discolored hair without leaving unnatural or unsatisfactory tones in the hair, such as blues or purples, but also presented a minimal risk of damage to hair that has undergone chemical processes such as relaxing or waving. Also surprising was the result of a noticeable absence of skin and scalp irritation, and the absence or minimal bleaching of the natural underlying color of the hair, even after later alkali relaxing or waving treatments.

In the most preferable embodiments of the invention, the active hair brightening ingredients comprised about 0.5 to 5 weight percent of the oxidizing salts of the invention, used alone or in combination with the colorant active ingredients at concentrations of about 0.00001 weight percent to about 0.3 weight percent colorant active ingredient, and most preferably 0.0001 to 0.05 weight percent. The most preferred oxidizing salts of the invention are sodium and potassium bromate, and potassium and sodium chlorate; the most preferred colorants are D&C Violet #2, External D&C Violet #2, FD&C Blue #1; and the preferred pH for the brightening compositions of the invention is in a range of about 2 to about 8.5, most preferably in a range of about 5 to about 7.

In one embodiment, the relaxing process of the present invention includes a first step in which a commercially available hair relaxing composition is applied to the hair fibers for an amount of time sufficient to at least partially relax the hair. Any commercially available hair relaxing composition may be used for this step, such as Affirm® Hair Relaxer (Avlon Industries, Bedford Park, Ill.). Thereafter, substantially all of the hair relaxing composition is removed by rinsing the relaxed hair with water. Next, an alkali neutralizing composition, generally in the form of a shampoo or conditioner, is applied to the rinsed hair. This alkali neutralizing composition typically has a pH of less than 8. After rinsing the substantially neutral relaxed hair with water, an aqueous hair brightening activating composition (such as the one set forth in Example 7, below) is applied in an effective brightening amount directly to the hair fibers that have been relaxed and discolored. This brightening composition remains on the hair for an amount of time suitable to brighten the hair and at least partly remove discolorations, generally in the range of one to twenty minutes (although brightening is immediately visible in most cases), and then the hair is rinsed with water for a time sufficient to remove the brightening composition. The hair may optionally be post-treated with one or more of the formulations of the invention, which is then rinsed from the hair.

In a variation of the foregoing embodiment, any one or more of the other brightening compositions shown in Examples 1–6 and 8–13 may be used at the appropriate step during the relaxing process following alkali neutralization of the hair, instead of or in addition to the hair brightening activator solution. In addition, because the brightening compositions of the invention provide the significant advantage of being less damaging than prior art brightening compositions, they may be applied for a second or third time if needed, or in more than one form if desired.

In an alternative embodiment, the neutralizing shampoo used may further comprise a shampoo composition of the invention (Examples 1, 5, 6, 8 and 11), eliminating the need for a separate hair brightening step wherein the hair brightening composition is applied post-neutralization. This neutralizing/brightening shampoo may optionally comprise blue or violet (or both) colorants. Also, other post neutralizing brightening compositions of the invention may optionally be used with the brightening shampoo.

In yet another preferred embodiment of the invention, hair brightening compositions may be applied in an effective amount to previously thiol waved hair fibers. First the hair is usually exposed to a reductive thiol wave composition for less than twenty-five minutes, preferably about eighteen to twenty-four minutes or as determined by the practitioner. Any commercially available waving solution may be used for this step of this invention. After the waved hair is rinsed with water, an oxidative neutralizer of a pH generally less than 8 is applied to the hair and the hair is then rinsed with water.

Thereafter, any of the hair brightening compositions of the invention (such as, but not limited to, those set forth in Examples 1–13) in an effective amount may be applied to and distributed throughout the neutralized waved hair fibers that are discolored. This application remains on the hair fibers for an amount of time sufficient to brighten the hair by removing at least part of the discoloration, generally in the range of one to twenty minutes, and the brightening composition is then removed by rinsing the hair fibers with water.

As shown in Table 1, below, because the hair brightening compositions of the invention provide the significant advantage of being less damaging than prior art brightening compositions, they may be applied for a second or third time if needed, or in more than one form if desired.

The hair brightening compositions of the invention preferably are at a physiologically tolerable pH in a range of about 5 to about 7. The specific pH of each hair brightening composition is determined by the active brightening agent selected, and the pH at which it is most effective cosmetically and most stable chemically.

The compositions employed were considered useful as a hair brightening agent of the invention if they removed the discolorations to at least a level intermediate between the discolored tone of the unbrightened hair and the corresponding tone of non-discolored hair. The most preferable brightening compositions resulted in a substantially more natural tone approximating or better than that of non-discolored hair. The materials selected as hair brightening agents were judged by viewing the total contact time required to brighten discolored alkali-relaxed or thiol-waved hair. The hair brightening compositions of the invention had a total contact time of less than about twenty minutes, preferably less than about ten minutes, more preferably about two to five minutes.

It is intended that within the scope of this invention as hair brightening agents are compositions which have an oxidizing power which is effective in brightening hair at concentration in water in a range of about 0.1 to about 10 weight percent, more preferably in a range of about 0.5 to about 5 weight percent, most preferably in a range of about 1 to about 3 weight percent.

Sodium bromate, and sodium chlorate in powder forms are particularly preferred as a hair brightening activator salt of the invention, based on convenience in handling and efficacy. These chemicals, and the other hair brightening activator salt agents of the invention, are well-known to practitioners of the art and readily available from a wide variety of conmmercial sources as stabilized concentrated aqueous liquids which may be diluted for use, or as powders which must be dissolved for use.

In practicing the compositions and processes; of the invention, the concentration of active hair brightener ingredient, most preferably sodium bromate or sodium chlorate or blue or violet dyes,(alone or in combination) present in hair brightener compositions is preferably at a concentration that is non-irritating to the skin and scalp. In addition, the brightener compositions are used under pH conditions where alkaline induced bleaching of hair is avoided or substantially minimal.

The contact time needed to produce hair brightening under practical conditions was determined by the volume of hair on the person's head, the length of time it takes to apply and distribute the hair brightener composition, the severity of the alteration to be corrected and the concentration and nature of the brightening agent used. It was determined that the hair brightener composition must only be in contact with the hair for as long as needed to sufficiently brighten the hair. Thus, brightening can be obtained in a total contact time of less than one minute to over twenty minutes, most frequently in less than about ten minutes. As the concentration of active brightening ingredient decreases or increases, the length of contact time needed correspondingly increases or decreases, respectively.

Any topical hair product, comprising gels, shampoos, emulsions, conditioners, lotions or sprays may incorporate the present hair brightening system effectively.

The following Examples are provided to illustrate preferred embodiments of shampoos and conditioners in accordance with the principles of the present invention, but are not to be construed as limiting the invention. In the Examples shown below, practitioners of the art will appreciate that sodium bromate may be optionally replaced with other hair brightening activator salts of bromate or salts of chlorate; and that hair brightening organic coloring agents can be used singly or in combinations. The preferred hair brightening activator salts of the invention are sodium salts, although potassium salts and the like are also useful so long as the salt is water-soluble, and does riot impart any unnatural coloration to the hair. The invention encompasses within its scope any such oxidizing salt which is safe and effective for cosmetic purposes so long as it is an active hair brightening ingredient in accordance with the principles of the invention. The preferred hair brightening organic coloring agents of the invention are D&C Violet #2, External D&C Violet #2 and D&C Blue #1 and mixtures thereof.

EXAMPLES 1–13

GENERAL FORMULAE FOR BRIGHTENING SHAMPOOS AND BRIGHTENING CONDITIONERS

Examples 1 & 2 set forth a preferred embodiment of the brightening shampoo and the brightening conditioner of the invention respectively, with the active brightening ingredient being sodium bromate in the conditioner (Ex. 2) and sodium bromate in combination with D&C Violet #2 and External D&C Violet #2 in the shampoo (Ex. 1).

| Brightening Shampoo | | Brightening Conditioner | |
|---|---|---|---|
| Component | Weight Percent | Component | Weight Percent |
| Phase A | | Phase A | |
| Deionized Water | Q.S. | Deionized Water | Q.S. |
| pH Adjusting Agent | 0.01–0.5 | Thickening Agent | 0.1–2 |
| D&C Violet #2 | 0.0001–0.5 | Preservatives | Q.S. |
| External D&C Violet #2 | 0.0001–0.5 | Chelating Agent | Q.S. |
| Phase B | | Plasticizer Agent | 0.1–8 |
| Preservatives | Q.S. | Antistatic Agent | 0.1–10 |
| Chelating Agent | Q.S. | Phase B | |
| Antistatic Agent | Q.S. | Emulsifying Agent | 0.1–20 |
| Foaming Agent | Q.S. | Conditioning Agent | 0.1–10 |
| Opacifier Agent | Q.S. | Organic Solvent | 0.1–10 |
| Phase C | | Phase C | |
| Conditioning Agent | Q.S. | Sodium Bromate | 0.5–3 |
| Fragrance | Q.S. | Stabilizer | Q.S. |
| Solubilizer | Q.S. | | |
| Sodium Bromate | 0.001–2 | | |
| Total | 100 | Total | 100 |

Preferred conditioning agents useful in these and the examples set forth below include, but are not limited to polymeric conditioning agents and non-polymeric proteinaceous conditioning agents.

Representative polymeric conditioning agents are: polyvinylpyrrolidone/dimethylaminoethylmethacrylate (one of which is sold under the tradename "Copolymer 845") copolymers of vinylpyrrolidone and methacrylamidopropyl trimethylammonium chloride (one of which is sold under the tradename "Gafquat HS-100"); quaternized copolymers of vinylpyrrolidone and dimethylaminoethyl methacrylate (one of which is sold under the tradename "Gafquat 755N"); copolymers of polydimethylsiloxane and polyvinylpyrrolidone (one of which is sold under the tradename "PVP/Si-10") (all four of the foregoing are commercially available from International Specialty Products (also known as "ISP," Wayne, N.J.); sodium polystyrene sulfonate (which is commercially available from National Starch under the tradename "Flexan-130"); and dimethyldiallylammonium chloride (commercially available under the trade name "Merquat 100" from Calgon).

Representative non-polymeric proteinaceous conditioning agents are: hydrolyzed keratin (commercially available from Croda under the tradename "Crotein K"); hydrolyzed pea protein (commercially available from Maybrook under the tradename "Pea Pro-Tein BK"); hydrolyzed rice protein (commercially available from Brooks under the tradename "Rice Pro EN-20"); hydrolyzed almond protein (commercially available from Silab under the tradename "Amanduline"); hydrolyzed vegetable protein (commercially available from Induchem under the tradename "Unipertan V-24"); hydrolyzed soy protein (commercially available from Croda under the tradename "Hydroso 2000/S.F.") and hydrolyzed wheat protein (commercially available from Croda under the tradename "Tritisol"). One preferred solubilizer is Polysorbate 20, which is well known. Carbomer 940 is a commercially available thickening agent from B. F. Goodrich (Akron, Ohio). PVP/VA Copolymer is a useful film forming hair styling polymer commercially available from BASF Corporation (Mt. Olive, N.J.).

In Example 2 and in other embodiments shown below, a sodium bromate stabilizer may optionally be added where a long shelf-life is desired. Azulene is one such preferred stabilizer which is well known to practitioners of the cosmetic arts. A preferred organic solvent is propylene glycol.

Examples 3, 4 and 12 below provide additional preferred embodiments of the brightening conditioner compositions of the invention, while Examples 9 and 10 provide additional preferred embodiments of general formulations of the brightening conditioners of the invention. Examples 5, 6 and 8 provide preferred embodiments of the brightening shampoo compositions of the invention while Example 11 provides an additional preferred embodiment of a general formulation of the brightening shampoo of the invention. Example 13 provides a preferred embodiment of a gel form of one of the brightening compositions of the invention and Example 17 provides a preferred embodiment for a relaxing kit for the hair brightening system of the invention. Other embodiments of invention comprising the active brightening ingredients disclosed herein are possible and are also considered within the scope of the invention.

Procedures for making the compositions set forth in examples 1–6 and 8–12 are set forth in Example 14.

EXAMPLE 3

| Brightening Conditioner | |
|---|---|
| Component | Weight Percent |
| Phase A | |
| Deionized Water | Q.S. |
| Polyquaternium-10 | 0.1–2 |
| Preservatives | Q.S. |
| Tetrasodium EDTA | Q.S. |
| Glycerine | 0.1–8 |
| Phase B | |
| Isostearyl Ethylimidonium Ethosulfate (10%) | 0.1–20 |
| Stearalkonium Chloride (12%) | 0.1–20 |
| Ceteth-20 | 0.1–1 |
| Mineral Oil | 0.1–10 |
| Fatty Alcohol | 0.1–10 |
| Benzyl Alcohol | 0.1–10 |
| Phase C | |
| Sodium Bromate | 0.5–2 |
| Stabilizer (optional) | 0.001–2 |
| D&C Violet #2 | 0.0001–0.15 |
| External D&C Violet #2 | 0.0001–0.15 |
| Total | 100 |

Polyquaternium-10 is one well-known preferred thickening and conditioning agent of the invention, although others may be used. Polyquaternum-10 is available under the trade name "Polymer JR-30M" from Amerchol Corporation, Edison, N.J. Isostearyl ethylimidonium ethosulfate is commercially available under the tradename "Monoquat ISIES" from Mona Industries, Inc. of Patterson, N.J.

In this Example 3, the D&C Violet #2 and External D&C Violet #2 may optionally be replaced by FD&C Blue #1. A preferred brightening conditioner contained 1.5% sodium bromate or sodium chlorate; 0.025% D&C Violet #2 and 0.027% External Violet #2 or 0.05% FD&C Blue #1.

EXAMPLE 4

Brightening Conditioner

| Component | Weight Percent |
|---|---|
| Phase A | |
| Deionized Water | Q.S. |
| Polyquaternium-10 | 0.1–2 |
| Preservatives | Q.S. |
| Tetrasodium EDTA | Q.S. |
| Glycerine | 0.1–8 |
| Isostearyl Ethylimidonium Ethosulfate (10%) | 0.1–20 |
| Phase B | |
| Stearalkonium Chloride (12%) | 0.1–20 |
| Ceteth-20 | 0.1–2 |
| Mineral Oil | 0.1–10 |
| Fatty Alcohol | 0.1–10 |
| Phase C | |
| Benzyl Alcohol | 0.1–10 |
| FD&C Blue #1 | 0.0001–0.2 |
| Total | 100 |

In Example 4, FD&C Blue #1 may optionally be replaced by D&C Violet #2 and External D&C Violet #2. Polyquaterrium-10 is one well-known preferred thickening and conditioning agent of the invention, although others may be used. A preferred brightening conditioner contained about 0.05% FD&C Blue #1 or a combination of about 0.025% D&C Violet #2 and about 0.027% External Violet #2.

EXAMPLE 5

Brightening Shampoo

| Component | Weight Percent |
|---|---|
| Phase A | |
| Deionized Water | Q.S. |
| Citric Acid | 0.01–0.5 |
| D&C Violet #2 | 0.0001–0.3 |
| Mineral Oil | 0.5–3 |
| External D&C Violet #2 | 0.0001–0.3 |
| Phase B | |
| Preservatives | Q.S. |
| Tetrasodium EDTA | 0.1–2 |
| Copolymer of vinylpyrrolidone and methacrylamidopropyl trimethylammonium chloride (20% in water) | 0.5–5 |
| Disodium Cocoamphodipropionate (40%) | 1–30 |
| Ammonium Lauryl Sulfate (30%) | 1–30 |
| Lauramide DEA (10%) | 1–20 |
| Glycol Stearate | 0.1–10 |
| PEG-120 Methyl Glucose Dioleate | 0.1–10 |
| Phase C | |
| Hydrolyzed Collagen (55%) | 0.1–4 |
| DMDM Hydantoin (55%) | 0.1–4 |
| Sodium Bromate | 0.5–5 |
| Azulene | 0.0001–2 |
| Polysorbate 20 | 0.1–4 |
| Fragrance | 0.01–1 |
| Total | 100 |

The copolymer in Example 5 is commercially available under the tradename "Gafquat HS-100" from ISP, Wayne, N.J. The hydrolyzed collagen is commercially available from Hormel Corporation, under the tradename "Peptein 2000."

Preferably, the brightening shampoo contains about 0.5% to about 1.5% sodium bromate (or sodium chlorate), about 0.025% D&C Violet #2 and about 0.027% External Violet #2.

EXAMPLE 6

Brightening Shampoo

| Component | Weight Percent |
|---|---|
| Phase A | |
| Deionized Water | Q.S. |
| Citric Acid | 0.01–0.5 |
| Preservatives | Q.S. |
| Tetrasodium EDTA | 0.1–2 |
| Phase B | |
| Copolymer of vinylpyrrolidone and methacrylamidopropyl trimethylammonium chloride (20%) | 1–5 |
| Disodium Cocoamphodipropionate (40%) | 5–20 |
| Ammonium Lauryl Sulfate (30%) | 3–30 |
| Lauramide DEA (10%) | 2–20 |
| Glycol Stearate | 0.1–5 |
| PEG-120 Methyl Glucose Dioleate | 0.2–5 |
| Phase C | |
| Hydrolyzed Collagen (55%) | 0.1–3 |
| DMDM Hydantoin (55%) | 0.1–2 |
| FD&C Blue #1 | 0.001–0.5 |
| Solubilizer | 0.1–2 |
| Fragrance | 0.1–2 |
| Total | 100 |

One preferred fragrance solubilizer is Polysorbate 20, which is well known to those in the cosmetic arts and available from a variety of sources.

The brightening shampoo is preferably mixed substantially immediately before use with a sufficient amount of brightening activator solution of Example 7 to effect hair brightening.

EXAMPLE 7

Brightening Activator Solution

| Component | Weight Percent |
|---|---|
| Sodium Bromate | 0.2–20 |
| Deionized Water | Q.S. to 100 |

Procedure: Dissolve sodium bromate in deionized water at room temperature until solution is homogeneously uniform.

At a concentration of sodium bromate in the range of about 0.2 to about 5 weight percent, preferably in the range of about 0.5 to about 2 weight percent, the brightening activator solution can be applied to the hair undiluted. At a concentration of sodium bromate above about 5 weight percent, the brightening activator provides a concentrated solution for economical stable storage that can be diluted substantially immediately before use to the desired hair brightening concentration. The brightening activator solution is preferably mixed with a brightening shampoo for use, such as the brightening shampoo described in Examples 5 or 6 for use in an amount sufficient to effect hair brightening. A preferred amount is about 1 part of brightening activator solution to about 10 parts of brightening shampoo to provide about 1 to about 2% sodium bromate. Alternatively, the brightening activator solution can be mixed with a brightening conditioner such as the brightening conditioner of Example 10 for use in an amount sufficient to effect hair brightening.

In the above Examples 1–7, sodium bromate may optionally be replaced by potassium bromate, sodium chlorate, potassium chlorate, or salts of sulfite, bisulfite, hydrosulfite (most preferably sodium salts of the above), as an active hair brightening activator salt ingredient.

EXAMPLE 8

Brightening Shampoo

| Component | Weight Percent |
|---|---|
| Phase A | |
| Deionized Water | Q.S. |
| Citric Acid | 0.01–0.5 |
| Preservatives | Q.S. |
| Tetrasodium EDTA | 0.1–2 |
| Phase B | |
| Copolymer of vinylpyrrolidone and Methacrylamidopropyl Trimethylammonium Chloride (20% in water) | 1–5 |
| Disodium Cocoamphodipropionate (40%) | 2–30 |
| Ammonium Lauryl Sulfate (30%) | 2–20 |
| Lauramide DEA (10%) | 1–6 |
| Glycol Stearate | 0.1–5 |
| PEG-120 Methyl Glucose Dioleate | 0.5–2 |
| Phase C | |
| Hydrolyzed Collagen (55%) | 0.1–3 |
| DMDM Hydantoin (55%) | 0.1–2 |
| Sodium Bromate | 0.5–5 |
| Azulene | 0.0001–2 |
| Polysorbate 20 | 0.1–1 |
| Fragrance | 0.1 to 0.5 |
| Total | 100 |

In the above example, sodium bromate may optionally be replaced by potassium bromate, potassium chlorate, or sodium chlorate, or salts of sulfite, bisulfite, hydrosulfite (most preferably sodium salts of the above).

Preferably, the brightening shampoo contains about 1 to about 5% sodium bromate or sodium chlorate.

EXAMPLE 9

Brightening Conditioner

| Component | Weight Percent |
|---|---|
| Phase A | |
| Deionized Water | Q.S. |
| Thickening Agent | 0.1–2 |
| Preservatives | Q.S. |
| Chelating Agent | Q.S. |
| Plasticizer Agent | 0.1–8 |
| Antistatic Agent | 0.1–5 |
| Phase B | |
| Emulsifier Agent | 0.1–10 |
| Conditioning Agent | 0.1–10 |
| Organic Solvent | 0.1–10 |

Brightening Conditioner -continued

| Component | Weight Percent |
|---|---|
| Phase C | |
| Fragrance | Q.S. |
| FD&C Blue #1 | 0.0001–0.3 |
| Total | 100% |

Polyquaternium-10 is one well-known preferred dual purpose thickening and conditioning agent of the invention, although others may be used. Preferred plasticizers are propylene glycol or glycerine. Propylene glycol can also be the organic solvent.

EXAMPLE 10

Brightening Conditioner

| Component | Weight Percent |
|---|---|
| Phase A | |
| Deionized Water | Q.S. |
| Thickening Agent | 0.1–2 |
| Preservatives | Q.S. |
| Chelating Agent | Q.S. |
| Plasticizer Agent | 0.1–8 |
| Antistatic Agent | 0.1–2 |
| Phase B | |
| Emulsifier Agent | 0.1–10 |
| Conditioning Agent | 0.1–10 |
| Organic Solvent | 0.1–10 |
| Phase C | |
| Fragrance | Q.S. |
| D&C Violet #2 | 0.0001–0.3 |
| External D&C Violet #2 | 0.0001–0.3 |
| Total | 100 |

The brightening conditioner preferably contains about 0.025% to about 0.05% D&C Violet #2 and about 0.027% to about 0.06% External D&C Violet #2. The brightening conditioner is preferably mixed substantially immediately before use with a sufficient amount of brightening activator solution of Example 7 to effect hair brightening.

EXAMPLE 11

Brightening Shampoo

| Component: | Weight Percent |
|---|---|
| Phase A | |
| Deionized Water | Q.S. |
| pH Adjusting Agent | 0.01–0.5 |
| Phase B | |
| Preservatives | Q.S. |
| Chelating Agent | Q.S. |
| Antistatic Agent | Q.S. |
| Foaming Agent | Q.S. |
| Opacifier Agent | Q.S. |

-continued

Brightening Shampoo

| Component: | Weight Percent |
|---|---|
| Phase C | |
| Conditioning Agent | Q.S. |
| Sodium Sulfite | 0.5–10 |
| Preservatives | Q.S. |
| Fragrance | Q.S. |
| Total | 100 |

In the above example, sodium sulfite may optionally be replaced by sodium or potassium bromate or sodium or potassium chlorate or salts of sulfite, bisulfite, or hydrosulfite (most preferably sodium salts of the above). Preferably, the brightening shampoo contains about 1 to about 3% of sodium sufite or sodium bisulfite or sodium hydrosulfite.

EXAMPLE 12

Brightening Conditioner

| Component: | Weight Percent |
|---|---|
| Phase A | |
| Deionized Water | Q.S. |
| Polyquaternium-10 | 0.1–2 |
| Preservatives | Q.S. |
| Tetrasodium EDTA | Q.S. |
| Glycerine | 0.1–8 |
| Isostearyl Ethylimidonium Ethosulfate (10%) | 0.1–20 |
| Phase B | |
| Stearalkonium Chloride (12%) | 0.1–20 |
| Ceteth-20 | 0.1–2 |
| Mineral Oil | 0.1–10 |
| Fatty Alcohol | 0.1–10 |
| Phase C | |
| Benzyl Alcohol | 0.1–10 |
| Sodium Chlorate | 0.5–10 |
| Total | 100 |

In the above example, sodium chlorate may optionally be replaced by potassium chlorate or salts of sulfite, bisulfite or hydrosulfite (most preferably sodium salts of the above). Preferably, the brightening conditioner contains about 1 to about 3% of sodium sulfite or sodium bisulfite or sodium hydrosulfite.

EXAMPLE 13

Brightening Gel

| Component | Weight Percent |
|---|---|
| Phase A | |
| Deionized Water | Q.S. |
| Carbomer 940 | 0.5–2 |
| Phase B | |
| Deionized water | 11 |
| PVP/VA Copolymer | 0.5–3 |

-continued

Brightening Gel

| Component | Weight Percent |
|---|---|
| Panthenol (50%) | 0.1–5 |
| Sodium Sulfite | 0.5–8 |
| Phase C | |
| Preservatives | 0.1–2 |
| Fragrance | Q.S. |
| Total | 100 |

Procedure:
1. Combine ingredients in phase A following supplier's directions for dispersing Carbomer 940 in water.
2. Combine ingredients in phase B to a homogeneous solution.
3. Slowly add phase B into phase A, stirring until a uniform gel forms.
4. Add phase C ingredients to the mixture of A and B and mix until uniformly dispersed in gel.

In the above example, sodium sulfite may optionally be replaced by sodium or potassium bromate, or by sodium or potassium chlorate or salts of sulfite, bisulfite or hydrosulfite (most preferably by sodiuin salts of the above).

Preferably the brightening gel contains about 1 to about 3% sodium sulfite, or sodium bisulfite, or sodium hydrosulfite.

EXAMPLE 14

This example illustrates general procedures for preparing the inventive hair brightening compositions of Examples 1–6 and 8–13. Each procedure sets forth one method of making the compositions of the invention, although different methods of making the compositions are possible and contemplated as within the scope of the invention. The component ingredients of the compositions set forth are well known to practitioners of the relevant art and all are readily available from a variety of well-known sources, although preferred suppliers are noted in some cases.

Brightening Shampoo: (Examples 1, 5, 6, 8, and 11)
1. Disperse the components of phase A. Add the components of phase B into phase A one by one and heat up phase A+B to about 60° C. while mixing until uniformly homogeneous and then cool phase A+B down to about 45° C.
2. Dissolve fragrance, if present, in solubilizer first. Add the solubilized fragrance mixture into the so-cooled phase A+B and then add the rest of the ingredients in phase C. and mix for about 20 minutes or until homogenous and then cool the homogeneous shampoo to about 25° C. The shampoos are preferably substantially opaque and homogeneous. Brightening Conditioner: (Examples 2, 3, 4, 9, 10, and 12)
1. Dissolve thickening agent in water at about 25° C. under mixing until uniform and then heat the uniform mix to a temperature of up to about 75–80° C. Add the rest of the components in phase A and mix until uniform and homogeneous.
2. Mix the phase B ingredients together and heat to a temperature of about 75–80° C. Continue mixing, while maintaining the foregoing temperature until the phase B is uniform. Slowly add phase B to phase A and continue mixing until uniform at about 75–80° C. Cool gradually to 25° C.

3. Add the components of phase C to the cooled phase A+B and mix until uniform and homogeneous.

The conditioners are preferably prepared in the form of emulsions, lotions and the like.

EXAMPLE 15

Salon Tests

Salon tests were performed employing African-American female subjects having gray hair (about 10–80% or more white fibers). The results showed that representative compositions of Examples 3, 4, 5, 8, 11 and 12 and combinations of Examples 6 and 7 and of Examples 10 and 7 could remove discolorations and brighten hair. The procedures for comparative half head studies (i.e., one of the inventive hair brightening product; applied to the hair on one side of the head and a commercial conventional brightening product applied to the hair on the opposing side) and for whole head salon studies using compositions of the invention are set forth below.

Each subject was first given her choice of alkali-relaxing product (lye type or no-lye type) applied according to the manufacturer's instructions. The relaxer was removed by rinsing with water, and the hair was washed twice with a normalizing shampoo to neutralize the residual alkali in the hair, and complete the alkali relaxing process. After the alkali relaxing process was completed and if the hair was judged visually discolored, a brightening composition of the invention was applied for a period sufficient to remove the discoloration and substantially restore a more natural tonal appearance to the hair. Shampoo compositions were applied to and distributed through the hair to contact the discolored fibers and lathered in the manner that shampoos conventionally are applied when washing the hair and then rinsed from the hair. Conditioner compositions were applied to the hair and distributed through the hair to contact the discolored fibers and then rinsed from ihe hair with water. For half-head comparison, a commercial product containing either hydrogen peroxide (such as Yellow-Out Conditioner, Johnson Products, Chicago, Ill. containing 1.15% hydrogen peroxide) or violet organic colorants, (such as Shimmering Light, Clairol, Inc., containing D&C Violet #2 and External D&C Violet #2) as the sole hair brightening ingredient were used.

The tonal appearance of the white fibers in gray hair was visually assessed by by the professional salon stylists and rated on a hair brightness scale of 1–4 defined and summarized as follows:

SCORE TONAL DISCOLORATION ON HAIR AND APPEARANCE

1 Yellowish, greenish, golden, very dull, (typically observed following conventional alkali relaxation)

2 Moderately yellowish, greenish, golden, dull, (typically observed following use of commercial violet organic colorant product)

3 Slightly yellowish, greenish, golden, generally shiny but some hair strands still visibly dull, (typically observed following use of commercial product containing hydrogen peroxide)

4 None, tone is completely clear, very shiny, (typically observed following use of inventive compositions containing sodium bromate and organic colorants)

In half-head studies of hair brightening conditioners of Example 3 containing 1.5% of either sodium bromate or sodium chlorate in combination either with 0.025% D&C Violet #2 and 0.027% External Violet #2 or 0.05% FD&C Blue #1, the inventive conditioners gave scores of 4, whereas the Yellow-Out conditioner product gave scores of 3 and the Shimmering Light gave scores of 2–2.5.

In whole-head studies, the hair brightening conditioners of Example 4, containing either 0.5% FD&C Blue #1 or a combination of 0.025% D&C Violet #2 and 0.027% External D&C Violet #2 gave scores of 3.

Half-head studies were made of hair brightening shampoos of Example 5, containing 0.025% D&C Violet #2 and 0.027% External D&C Violet #2 and either (A) 0.5%; (B) 1.15%; or (C) 1.5% sodium bromate concentrations. Shampoo (A) scored a 3, and shampoos (B) and (C) each gave scores of 4, whereas the Yellow-Out conditioner product gave scores of 3.5 and the Shimmering Light product gave scores of 2.5. Similar hair brightening shampoos of Example 5 containing either 1.15% or 1.5% sodium chlorate also gave scores of 4.

In half-head studies with the brightener shampoo of Example 8 at a concentration of either sodium bromate or sodium chlorate of (A) 2%, (B) 3% or (C) 5%, the sodium bromate shampoos (A), (B), and (C) each gave scores of 3. The sodium chlorate shampoo (A) scored a 3, (B) gave a score of 3.5 and (C) scored a 4. The Yellow-Out conditioner product gave a score of 3.

In whole-head studies, brightener shampoos of Example 11 containing either (A) 1% or (B) 3% of either sodium sulfite, sodium bisulfite or sodium hydrosulfite were tested. Sodium sulfite and sodium bisulfite shampoos gave scores of 3.5 at both concentrations. Sodium hydrosulfite gave a score of 3 at the 1% concentration and of 3.5 at the 3% concentration. This same effect was also seen in whole-head studies of brightener conditioners of Example 12 containing 1% or 3% sodium hydrosulfite.

Half-head studies were made of brightener conditioners of Example 12, containing either 1% or 3% of either sodium chlorate, or sodium sulfite or sodium bisulfite. Sodium chlorate scored a 3 at 1% and scored a 3.5 at 3%. Both the sodium sulfite and sodium bisulfite at either concentration gave a score of 3.5. In all studies, the Yellow-Out conditioning product gave scores of 3 and the Shimmering Light product gave a score of 2.5.

The foregoing salon studies also demonstrated the surprising finding that greater hair brightening was achieved when sodium bromate was used in combination with the organic colorant than when either the sodium bromate or organic colorant was the sole hair brightening agent.

Use of the Brightening Activator solution of Example 7, used in combination with the Brightening Shampoo of Example 6 to provide 1% sodium bromate and 0.5% FD&C Blue #1 gave a score of 4 in whole-head tests. Also, the combination of Brightening Activator solution of Example 7 and the brightening conditioner of Example 10 containing either 1% sodium bromate, 0.025% D&C Violet #2, and 0.027% External D&C Violet #2 or 2% sodium bromate, 0.05% D&C Violet #2 and 0.06% External Violet #2 each gave scores of 4.

In salon studies, by the time the hair brightener compositions of the invention were applied to and distributed through the hair (particularly through the discolored portions), the tone of the hair was visibly and desirably brightened to a tone substantially near to natural. Discolored fibers were generally brightened, and their natural attractive bright highlights were restored. The results were judged visibly dramatic and superior in brightening efficacy to those of the commercially available products.

EXAMPLE 16

Comparison Study of Tensile Strength of Hair Fibers Using Brighteners

Measurements of hair tensile properties were made to assess the strength of alkali relaxed hair fibers brightened in accordance with the methods and compositions of the invention versus alkali relaxed hair fibers brightened in accordance with commercially available hydrogen peroxide-based brighteners. These measurements surprisingly showed that the brightening composition of the invention caused less damage to the hair than conventional hydrogen peroxide-based brighteners.

48 Hair fibers (virgin, natural brown hair, DeMeo Brothers) with known similar diameters of 85 to 90 Micrometers were each treated by applying Avlon's Affirm® Original Formula Normal Strength relaxer containing about 2–2.2% sodium hydroxide for about eighteen minutes and the alkali relaxer then 5 was rinsed off with deionized water. Avlon's Affirm®Normalizing Shampoo then was applied to each of the relaxed hair fibers and then was rinsed off with water. These alkali relaxed treated fibers were then immersed in deionized water set at a temperature of about 21° C. for about thirty minutes. The work required for achieving 20% elongation (F-20 index) tensile strength property was determined with the fibers immersed in water set at a controlled temperature of about 21° C. and a humidity of about 65% using Dia-Stron MTT set at the following parameters:

| | |
|---|---|
| Range | 50.0 grams |
| Gauge | 2.0 grams |
| Sample Size | 30.0 mm |
| Phase 1 | 20.0% |
| Phase 2 | 0.0 sec. |
| Phase 3 | 0.0% |
| Phase 4 | 0.0 sec. |
| Speed | 10.0 mm/min. |
| No. of Cycles | 1 Cycles |

One set of 24 alkali relaxed hair fibers (sample #'s 1–24) were then each treated using about 5 grams of a Hair Brightening Shampoo of Example 5 containing about 1.15% sodium bromate, about 0.025% D&C Violet #2 and about 0.027% External D&C Violet #2. This set is referred to herein as "Brightening Shampoo and Activator Treatment." The hair brightening shampoo and activator treatment was applied to the fibers for about 5 minutes and then rinsed off with water.

The remaining 24 alkali relaxed hair fibers (sample #'s 25–48) were each similarly treated employing about 5 grams of a commercial hydrogen peroxide-based product (Yellow-Out Conditioner, commercially available from Johnson Products, Chicago, Ill.) comprising 1.15% hydrogen peroxide for 5 minutes and then rinsed off with water. This set is referred to herein as "Yellow-Out Product Treatment."

All of the 48 test hair fibers were left in plates at ambient room temperature (25° C.) and relative humidity (about 65%) overnight and were then immersed in deionized water for 30 minutes. Their tensile strength F-20 indices were determined again using the Dia-Stron MTT. The comparative tensile strength results of this test can be seen in Table 1 below:

TABLE 1

Comparison Study of Tensile Strength Loss

| | F-20 Work(mjoul) | | F-20 Work(mjoul) Loss | |
|---|---|---|---|---|
| Sample No. | Before Treatment | Afer Treatment | Difference | Difference (%) |
| Brightening Shampoo and Activator Treatment | | | | |
| 1 | 1.36E-03 | 1.31 E-03 | 5.00E-05 | 3.68E+00 |
| 2 | 6.40E-04 | 6.21E-04 | 1.90E-05 | 2.97E+00 |
| 3 | 8.83E-04 | 8.79E-04 | 4.00E-06 | 4.53E-01 |
| 4 | 1.19E-03 | 1.14E-03 | 5.00E-05 | 4.20E+00 |
| 5 | 1.10E-03 | 1.07E-03 | 3.00E-05 | 2.73E+00 |
| 6 | 1.02E-03 | 1.02E-03 | 0.00E+00 | 0.00E+00 |
| 7 | 1.05E-03 | 1.03E-03 | 2.00E-05 | 1.90E+00 |
| 8 | 9.95E-04 | 9.86E-04 | 9.00E-06 | 905E-01 |
| 9 | 1.00E-03 | 9.94E-04 | 6.00E-06 | 6.00E-01 |
| 10 | 9.56E-04 | 9.32E-04 | 2.40E-05 | 2.51 E+00 |
| 11 | 1.13E-03 | 1.01E-03 | 1.20E-04 | 1.06E+01 |
| 12 | 6.57E-04 | 6.52E-04 | 5.00E-06 | 7.61 E-01 |
| 13 | 8.55E-04 | 8.37E-04 | 1.80E-05 | 2.11 E+00 |
| 14 | 1.00E-03 | 9.88E-04 | 1.20E-00 | 1.20E+00 |
| 15 | 1.33E-03 | 1.29E-03 | 4.00E-05 | 3.01 E+00 |
| 16 | 9.42E-04 | 9.23E-04 | 1.90E-05 | 2.02E+00 |
| 17 | 1.10E-03 | 1.04E-03 | 6.00E-05 | 5.45E+00 |
| 18 | 8.74E-04 | 8.67E-04 | 7.00E-06 | 8.01 E-01 |
| 19 | 7.15E-04 | 7.05E-04 | 1.00E-05 | 1.40E+00 |
| 20 | 8.28E-04 | 8.18E-04 | 1.00E-05 | 1.21 E+00 |
| 21 | 9.45E-04 | 9.37E-04 | 8.00E-06 | 8.47E-01 |
| 22 | 1.06E-03 | 9.67E-04 | 9.30E-05 | 8.77E+00 |
| 23 | 8.60E-04 | 8.54E-04 | 6.00E-06 | 6.98E-01 |
| 24 | 8.65E-04 | 8.29E-04 | 3.60E-05 | 4.16E+00 |
| Average | | | | 2.62E+00 |
| Standard Deviation | | | | 2.54 |
| t-value | | | | −4.29 |
| Yellow-Out Product Treatment | | | | |
| 25 | 7.57E-04 | 7.38E-04 | 1.90E-05 | 2.51E+00 |
| 26 | 4.90E-04 | 4.69E-04 | 2.10E-05 | 4.29E+00 |
| 27 | 4.22E-04 | 3.85E-04 | 3.70E-05 | 8.77E+00 |
| 28 | 8.11 E-04 | 7.68E-04 | 4.30E-05 | 5.30E+00 |
| 29 | 6.59E-04 | 6.19E-04 | 4.00E-05 | 6.07E+00 |
| 30 | 4.89E-04 | 4.67E-04 | 2.20E-05 | 4.50E+00 |
| 31 | 5.73E-04 | 5.24E-04 | 4.90E-05 | 8.55E+00 |
| 32 | 5.96E-04 | 5.37E-04 | 5.90E-05 | 9.90E+00 |
| 33 | 6.77E-04 | 6.33E-04 | 4.40E-05 | 6.50E+00 |
| 34 | 6.78E-04 | 6.37E-04 | 4.10E-05 | 6.05E+00 |
| 35 | 8.10E-04 | 7.39E-04 | 7.10E-05 | 8.77E+00 |
| 36 | 5.16E-04 | 5.09E-04 | 7. 00E-0 | 61.36E+00 |
| 37 | 5.59E-04 | 5.42 E-04 | 1.70E-05 | 3.04E+00 |
| 38 | 7.19E-04 | 6.89E-04 | 3.00E-05 | 4.17E+00 |
| 39 | 1.07E-03 | 9.68E-04 | 1.02E-04 | 9.53E+00 |
| 40 | 7.09E-04 | 6.89E-04 | 2.00E-05 | 2.82E+00 |
| 41 | 971E-04 | 8.78E-04 | 9.30E-05 | 9.58E+C0 |
| 42 | 5.84E-04 | 5.54 E-04 | 3.00E-05 | 5.14E+00 |
| 43 | 4.83E-04 | 4.69E-04 | 1.40E-05 | 2.90E+00 |
| 44 | 4.84E-04 | 4.37E-04 | 4.70E-05 | 9.71 E+00 |
| 45 | 6.82E-04 | 6.58E-04 | 2.40E-05 | 3.52E+00 |
| 46 | 6.18E-04 | 5.79E-04 | 3.90E-05 | 6.31 E+00 |
| 47 | 5.07E-04 | 4.86E-04 | 2.10E-05 | 4.14E+00 |
| 48 | 1.11E-03 | 1.05E-03 | 6.00E-05 | 5.41E+00 |
| Average | | | | 5.78E+00 |
| Standard Deviation | | | | 2.59 |

The results showed that the hair brightening shampoo of the invention containing 1.15% sodium bromate has significantly less loss of hair strength than at least one commercially available hydrogen peroxide-based brightening product with 1.15% hydrogen peroxide. The difference of F-20 loss between the hair brightener of the invention and the hydrogen peroxide-based brightener was judged statistically significant (at a confidence level of 95%). That is, the sodium bromate containing brightening composition has done less damage to the alkali relaxed hair than the hydrogen peroxide-based brightener at the same concentration level.

EXAMPLE 17
Single-Use Hair Relaxing Kit with Hair Brightener System

A preferred alkali hair relaxing kit embodiment for single use (one time), can comprise in separate packages, an alkali hair relaxing component (which may be either a single-part alkali relaxer or a 2-part alkali no-lye type relaxer component) and one or more of the hair brightener compositions described in Examples 1–13, individually packaged in single-use portions which are removably affixed in a single outer container. In addition, the kit may further comprise one or more of the following single-use components: conditioner, shampoo (which may be a normalizing neutralizing shampoo), hair protectorant (such as Preservo™ by Avlon Industries, Bedford Park, Ill.) or lotion components. All of the kits of the invention may further optionally contain one or more of the following: one or more applicators, one or more hair covers, gloves, cotton rope, a comb and a single-use portion of a skin protectorant component such as petroleum jelly.

EXAMPLE 18

The inventive hair brightening compositions were evaluated in lab bench studies employing tresses (2.5 gram each) of gray (about 75% white fibers) Caucasian hair fibers that were discolored by alkali relaxing (with lye-type or no lye-type relaxer); and then shampooed with normalizing shampoo twice to neutralize the alkali on the hair. The neutralized alkali relaxed tresses were treated with hair brightener compositions of the invention for 5 minutes; followed by water rinsing. The hair brightening was scored by professional salon stylists according to the visual scale described in Example 15.

Hair brightening compositions of Example 3, 4, 5, 8, 11 and 12 corresponding to those which were later salon tested as described in Example 15, produced the same brightening score values in lab bench studies as obtained in salon tests.

A hair brightening shampoo of Example 6 containing either 0.5% or 1.5% FD&C Blue #1 gave a score of 3 but some blue coloration was observed on the hair at the 1.5% level. The same result was obtained when a brightener conditioner of Example 9 was similarly evaluated.

Hair brightening scores obtained with hair brightener gels of Example 13 containing either 1% or 3% sodium sulfite or sodium bisulfite were 3.5. Hair brightening scores for hair brightener gels of Example 13 containing sodium hydrosulfite at a 1% concentration were 3 and at a 3% concentration were 3.5.

In accordance with the invention, we have disclosed novel hair brightening compositions and methods that brighten hair, particularly alkali relaxed hair, which has been previously discolored. We have further shown that the hair brightening compositions of the invention are less damaging to allkali relaxed hair than are commercially available hair brightener products comprising hydrogen peroxide, and we have shown that the hair brightening compositions of the invention are more effective per amount of active ingredient than commercially available hydrogen peroxide-based products.

The present invention has been described generally and with respect to certain embodiments and conditions, which are not meant to and should not be construed to limit the invention. Those skilled in the art will understand that variations from the embodiments and conditions described herein may be made without departing from the spirit and scope of the novel concept of the invention as described in the appended claims.

We claim:

1. A process for brightening discolored alkali-relaxed hair from having a discolored tone to a substantially natural tone comprising the steps of:
   (i) providing hair which has been discolored from an alkali-relaxing process;
   (ii) applying to the discolored alkali-relaxed hair an effective hair brightening amount of an aqueous hair brightening composition comprising water having dissolved therein on a total composition basis (a) about 0.001 to about 10 weight percent of a hair brightening activator salt selected from the group consisting of alkali metal salts of bromate, chlorate, sulfite, bisulfite and hydrosulfite; and (b) about 0.00001 to about 1 weight percent of an organic colorant selected from the group consisting of anthraquinone and triphenylmethane colorants and mixtures thereof;
   (iii) distributing the so-applied hair brightening composition through the discolored hair and leaving the hair brightening composition in contact therewith for a time period sufficient to visibly brighten the tone of said hair; and
   (iv) water rinsing the hair brightening composition from the so-brightened hair.

2. The process according to claim 1 wherein the time period in step (iii) is in the range of about 1 to about 20 minutes.

3. The process according to claim 1 wherein the hair brightening activator salt in the hair brightening composition has an alkali metal cation selected from the group consisting of sodium and potassium.

4. The process according to claim 1 wherein the concentration of the hair brightening activator salt in the hair brightening composition is in the range of about 1 to about 5 weight percent.

5. The process according to claim 4 wherein the concentration of the hair brightening activator salt in the hair brightening composition is sodium bromate at a concentration of about 1 to about 2 weight percent.

6. The process according to claim 1 wherein the brightening composition has a physiologically tolerable pH of less than about 9.

7. The process according to claim 1 wherein the brightening composition has a physiologically tolerable pH in the range of about 5 to about 7.

8. The process according to claim 1 wherein the anthraquinone organic colorants are selected from the group consisting of D&C Violet #2 (C.I. 60,725), and External D&C Violet #2 (C.I. 60,730), and the triphenylmethane organic colorant is FD&C Blue #1 (C.I. 42,090).

9. The process of claim 1 wherein the concentration of organic colorant in the hair brightening composition is in the range of about 0.0001 to about 0.75 weight percent.

10. The process of claim 1 wherein in the hair brightening composition the concentration of the hair brightening activator salt is in the range of about 1 to about 2 weight percent and the organic colorant is the range of about 0.01 to about 0.05 weight percent.

11. The process according to claim 1 wherein the hair brightening composition is applied in the form of a shampoo, emulsion, lotion, activator solution, conditioner, creme, or gel.

12. A process for brightening hair susceptible to discoloration during an alkali relaxing process comprising the steps of:
   (i) applying an alkali relaxer to the hair in a hair relaxing amount and for a time period sufficient to provide alkali-relaxed hair whose tone is visibly discolored sufficient to be in need of brightening;

(ii) removing the alkali relaxer from the alkali relaxed hair by rinsing with water;

(iii) neutralizing all residual alkalinity in the alkali relaxed, rinsed hair by applying an alkali neutralizing composition having a pH of less than 8 and removing the alkali neutralizing composition from the hair by rinsing with water;

(iv) removing discoloration from the rinsed, neutralized alkali relaxed hair by applying to the discolored portion of the hair an effective hair brightening amount of an aqueous hair brightening composition comprising water having dissolved therein on a total composition basis (a) about 0.001 to about 10 weight percent of a hair brightening activator salt selected from the group consisting of alkali metal salts of bromate, chlorate, sulfite, bisulfite, and hydrosulfite; and (b) about 0.00001 to about 1 weight percent of an organic colorant selected from anthraquinone and triphenylmetharLe colorants and mixtures thereof;

(v) distributing the so-applied hair brightening composition through the discolored hair portion and leaving the hair brightening composition in contact therewith for a time period sufficient to visibly brighten the tone of the so-contacted hair; and (vi) water rinsing the hair brightening composition from the so-brightened hair, such that the tone of the alkali relaxed hair after step (vi) is substantitally more natural than before step (iv).

13. The process of claim 12 further including the step of applying an effective hair conditioning amount of a hair conditioner between step (ii) and step (iii).

14. The process of claim 12 wherein component (a) of the hair brightening composition comprises about 1 to about 2 weight percent sodium bromate and component (b) comprises about 0.01 to about 0.05 weight percent organic colorant selected from the group consisting of D&C Violet #2 (C.I. 60,725), External D&C Violet #2 (C.I. 60,730), and FD&C Blue #1 (C.I. 42,090) and mixtures thereof.

15. A process for alkali relaxing of hair susceptible to discoloration thereby and substantially simultaneously brightening and neutralizing the alkali relaxed hair comprising the steps of:

(i) applying an alkali relaxer to the hair in a hair relaxing amount and for a time period sufficient to provide alkali-relaxed hair whose tone is visibly discolored sufficient to be in need of brightening;

(ii) removing the alkali relaxer from the alkali relaxed hair by rinsing with water;

(iii) substantially simultaneously neutralizing all residual alkalinity on and removing discoloration from the so rinsed alkali relaxed hair by applying thereto an effective neutralizing and hair brightening amount of an aqueous hair brightening composition comprising water having dissolved therein on a total composition basis (a) about 1 to about 10 weight percent of a hair brightening activator salt selected from the group consisting of alkali metal salts of bromate, chlorate, sulfite, bisulfite, and hydrosulfite; (b) about 0.01 to about 0.05 weight percent of an organic colorant selected from anthraquinone and triphenylmethane colorants and mixtures thereof; and having a physiologically tolerable pH in a range of about 5 to about 7;

(iv) distributing the so-applied hair brightening composition through the discolored hair and leaving the hair brightening composition in contact therewith for a time period sufficient to visibly brighten the tone of the hair; and (v) water rinsing the hair brightening composition from the so-brightened hair, such that the tone of the alkali relaxed hair after step (v) is substantially more natural than before step (iii).

16. The process of claim 15 including the further step of applying an effective hair conditioning amount of hair conditioner to the so-brightened hair.

* * * * *

UNITED STATES PATENT AND TRADEMARK OFFICE
CERTIFICATE OF CORRECTION

PATENT NO : 6,007,585
DATED : December 28, 1999
INVENTOR(S): Ali N. Syed, Wagdi W. Habib It is certified that error appears in the above-identified patent and that said Letters Patent is hereby corrected as shown below:

Column 7, line 12, change "secord" to read --second--.

Column 8, line 54, change "riot" to read --not--.

Column 9, line 5, insert --EXAMPLE 1-- above "Brightening Shampoo" and insert --EXAMPLE 2-- above "Brightening Conditioner".

Signed and Sealed this

Sixth Day of February, 2001

*Attest:*

Q. TODD DICKINSON

*Attesting Officer*   *Director of Patents and Trademarks*